United States Patent [19]
Ross et al.

[11] Patent Number: 6,133,233
[45] Date of Patent: *Oct. 17, 2000

[54] PEPTIDE MODULATION OF REPERFUSION INJURY

[75] Inventors: Christopher R. Ross; Frank Blecha, both of Manhattan, Kans.; Jishu Shi, Los Angeles, Calif.

[73] Assignee: Kansas State University Research Foundation, Manhattan, Kans.

[*] Notice: This patent issued on a continued prosecution application filed under 37 CFR 1.53(d), and is subject to the twenty year patent term provisions of 35 U.S.C. 154(a)(2).

[21] Appl. No.: 09/024,975

[22] Filed: Feb. 16, 1998

Related U.S. Application Data

[63] Continuation-in-part of application No. 08/802,306, Feb. 18, 1997, abandoned.

[51] Int. Cl.$^7$ .................................................. A61K 38/16
[52] U.S. Cl. .................... 514/12; 514/2; 514/12; 514/13; 514/14; 514/18; 530/324; 530/330
[58] Field of Search .................... 514/2, 12–14, 514/16, 18

[56] References Cited

U.S. PATENT DOCUMENTS 5,489,575  2/1996  Lee et al. .................................. 514/12
5,633,229  5/1997  Kokryakov et al. ...................... 514/12
5,654,273  8/1997  Gallo et al. .............................. 514/12

FOREIGN PATENT DOCUMENTS 2285047  6/1995  United Kingdom .

OTHER PUBLICATIONS

Ginis, I. et al. J. Cell. Physiol., 157: 569–578, Mar. 1993.

*Primary Examiner*—Michael P. Woodward
*Assistant Examiner*—Michael Borin
*Attorney, Agent, or Firm*—Hovey, Williams, Timmons & Collins

[57] ABSTRACT

An in vivo method of reducing reperfusion injury in a mammal resulting from reperfusion of a temporarily occluded blood vessel which comprises the steps of administering into the mammal's bloodstream an effective amount of a proline /arginine rich peptide such as PR-39 (SEQ ID NO: 1). The method has particular application in surgical procedures such as coronary bypass and organ transplantation surgery and where reperfusions occur subsequent to a spontaneous occlusion. Preferred peptides have up to about 50 amino acid residues with a plurality of —PXXP— sequences.

13 Claims, 10 Drawing Sheets

PR-39
RRRPRPPYLPRPRPPPFFPPRLPPRIPPGFPPRFPPRFP

Bac5
RFRPPIRRPPIRPPFYPPFRPPIRPPIFPPIRPPFRPPLGPFP rPR-26
IRPPLRPPFFPPPRPRPLYPPRPRRR

Bac7$_{(18+YC)}$
RRIRPRPPRLPRPRPRPLYC

C7
RRGPRHPQTRLPRPLPDP

PF-1$_{(1-21)}$
AFPPPNVPGPRFPPPNFPGPR

PR-39       RRRPRPPYLPRPRPPPFPPRLPPRIPPGFPPRFPPPRFP

Bac5        RFRPPIRRPPIRPPFYPPFRPPIRPPIFPPIRPPFRPPLGPFP rPR-26      IRPPLRPPFFPPPRPRPLYPPPRPRR

Bac7(18+YC) RRIRPRPPPRLPRPRPRPLYC

C7          RRGPRHPQTRLPRPLPDP

PF-1(1-21)  AFPPPNVPGPRFPPPNFPGPR

Fig. 5

*Different from 100%,

PEPTIDE MODULATION OF REPERFUSION INJURY

RELATED APPLICATION

This is a continuation-in-part of application Ser. No. 08/802,306, filed Feb. 18, 1997, now abandoned.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention is broadly concerned with an in vivo method of reducing reperfusion injury in a mammal resulting from temporary occlusion of a blood vessel and subsequent reperfusion thereof; the method comprises administration of certain proline and arginine-rich peptides to the mammal's bloodstream which lessen the potentially damaging effect of reperfusion. More particularly, the invention pertains to such a method wherein, in preferred forms, peptides having up to about 50 amino acid residues therein and one or more amino acid sequences —PXXP— where P is proline and X is any amino acid are administered to the bloodstream of a mammal so as to effectively contact the blood vessels and inhibit indices of reperfusion injury, i.e., production of reactive oxygen species, neutrophil adherence to endothelium and extravasation of neutrophils as a result of reperfusion.

2. Description of the Prior Art

In the course of some surgical procedures such as coronary bypass and organ transplantation surgery, blood vessels are intentionally occluded to allow the surgeon free access to the surgical site, whereupon the occlusion is removed and reperfusion of blood occurs. In addition, some patients with coronary or peripheral vascular disease are exposed to regular ischemia-reperfusion cycles (angina pectoris or intermittent claudication) that terminates spontaneously or in response to administered drugs. In this connection, it has been found that reperfusion is the cause of tissue damage, i.e., ischemic tissue prior to reperfusion is essentially undamaged, but will often experience massive, irreversible degradation such as cell death and tissue necrosis upon reperfusion. It is believed that the readmission of blood and oxygen during reperfusion promotes the release of oxygen-derived free radicals, and that this mechanism is a prime cause of tissue damage. Ischemia also disrupts the handling of oxygen by the mitochondrial electron transport systems and enzymes such as xanthine oxidase. Upon reperfusion, there is a rapid increase in free radical activity, probably amplified by transition metal ions released by ischemic cells. Subsequent damage to the sarcoplasmic reticulum and other membranes impairs handling of calcium and other ions, a hallmark of reperfusion injury. It has also been observed that reperfusion injury may occur over a period of several days (up to 5 days) time after reperfusion is begun, with the most extensive tissue damage occurring within the first 1–2 days. After blood flow has continued for 5 days, the reperfusion event is generally deemed concluded, and subsequent blood flow does not cause additional tissue damage.

Thus, reperfusion of tissues following ischemia leads to an array of biochemical events which can culminate in oxidative damage to cell structures. It is believed that reactive oxygen species such as superoxide ion are central to these events. It is also known that a major source of reactive oxygen intermediates are neutrophils.

PCT Publication WO 96/09322 entitled *Synducin Mediated Modulation of Tissue Repair* describes the use of PR-39 and related peptides for inducing the expression of proteoglycans, called syndecans, in mesenchymal cells. The reference suggests that the peptides can be administered after tissue death due to starvation in order to promote neovascularization. Accordingly, this reference postulates that damaged tissues can be partially restored via neovascularization long after ischemic damage and tissue death occurs. However, there is no suggestion of prevention or amelioration of reperfusion injury by any means; moreover, the reference does not teach administration of peptides into the bloodstream.

There is accordingly a need in the art for an in vivo method of reducing the extent of reperfusion injury which would otherwise result from reperfusion of a temporarily occluded mammalian blood vessel.

SUMMARY OF THE INVENTION

The present invention provides a new in vivo method of reducing reperfusion injury in a mammal (e.g., domestic or laboratory animals and man) resulting from the reperfusion of temporarily occluded blood vessels of the mammal. The method includes the steps of administering into the mammal's bloodstream prior to and/or during reperfusion of a temporarily occluded blood vessel a reperfusion injury-reducing amount of a proline/arginine-rich peptide, and allowing the peptide to come into effective contact with the blood vessel tissue for minimizing reperfusion injury. It has been found that a peptide having up to about 50 amino acid residues with at least about 60% of such residues made up of proline and arginine residues (i.e., both proline and arginine residues are present, and the total thereof constitutes up to about 60% of the total number of residues present in the peptide) can be used to good effect in the invention.

In preferred forms, the peptide should have at least about 65% thereof made up of proline and arginine (and most preferably from 65–80%). The preferred peptides are selected from the group consisting of the peptides of SEQ ID NOS: 1–11, with the more preferable peptides being those of SEQ ID NOS: 1–2; the single most preferred peptide is PR-39 (SEQ ID NO: 1). SEQ ID NOS: 1–11 have the following percentages of proline and arginine therein: NO: 1 (29/39), 74%; NO:2 (20/26), 77%; NO: 3 (12/16), 75%; NO: 4 (12/14), 86%; NO: 5 (5/7), 71%; NO: 6 (6/8), 75%; NO: 7 (39/54), 67%; NO. 8 (20/26), 77%; NO: 9 (15/20), 75%; NO: 10 (11/18), 61%; and NO: 11 (12/21), 57%. These preferred peptides lessen the known indicia of reperfusion injury, and a number also have a significant antibacterial capability. Certain of the preferred peptides are disclosed and described in PCT Publication No. WO 96/32129 which is incorporated by reference herein.

A further structural analysis of the operable peptides reveals that they should have at least one sequence —PXXP— therein where P is a proline residue and X is any amino acid residue; more preferably, at least four such —PXXP— sequences are present, and most preferably at least six such sequences. Advantageously, at least some of the multiple —PXXP— sequences are substantially contiguous, i.e., the terminal proline residue of one —PXXP— sequence is adjacent or within one or two residues of the initial proline residue of the next —PXXP— sequence. Finally, the peptides should have one or more basic residues within six residues (and preferably within three residues) from both the starting and terminal proline residues of the —PXXP— sequence. Thus, the peptide should contain a sequence $X_1X_2X_3X_4X_5X_6PXXPX_7X_8X_9X_{10}X_{11}X_{12}$— where some or all of the $X_1$–$X_{12}$ amino acid residues, inclusive, are basic residues. In like manner where plural —PXXP— sequences are present either contiguously or separated only by 1 or 2 residues, thus presenting a —PXXP— motif, one or more basic residues are present within the six (and preferably three) residues preceding and following the initial and terminal proline residues of the motif, respectively.

The concept of the —PXXP— structure is supported by an extensive literature, and this is considered to be a consensus sequence for binding to SH3 domains contained in many proteins (Ren, et al., (1993) Identification of a ten-amino acid proline-rich SH3 binding site. *Science* 259:1157–1116; Yu, et al., (1994) Structural basis for the binding of proline-rich peptides to SH3 domains. *Cell* 76:933–945; Feng, et al., (1994) Two binding orientations for peptides to the Src SH3 domain: Development of a general model for SH3-ligand interactions. *Science* 266:1241–1247; Sparks, et al., (1994) Identification and characterization of Src SH3 ligands from phage-displayed random peptide libraries. *J Biol Chem.* 269:23853–23856; Alexandropoulos, et al., (1995) Proline-rich sequences that bind to Src homology 3 domains with individual specificities. *Proc. A Nat. Acad Sci.* 92:3110–3114; Sparks, et al., (1995) Screening phage-displayed random peptide libraries for SH3 ligands. *Meth. Enzymol* 255:498509; Feng, et al., (1996) Bovine Natural Resistance Associated Macrophage Protein I (Nrampl) Gene. *Genome Research* 6:956–964; and Yamabhai, M, B Kay (1997) Examining the specificity of Src Homology 3 domain-ligand interactions with alkaline phosphatase fusion proteins. *Anal Biochem.* 247:143–151.

The amount of peptide used can vary depending upon the specific identity of the peptide, the type of surgical procedure or condition of the mammal and other relevant considerations.

The invention finds particular utility in connection with surgical procedures such as coronary bypass and organ transplantation surgery and in such cases, the peptides would normally be administered prior to the procedure. However, it may also be used prior to or during reperfusion after a spontaneous ischemic event. Examples of the latter situation include but are not limited to patients subject to coronary occlusion and stroke.

In the most preferred form of the invention, the peptides are administered prior to reperfusion, typically by a single infusion of the peptides into the bloodstream. Less desirably, the peptides may be administered during reperfusion and prior to termination of tissue damage owing to the reperfusion procedure. If the peptides are initially administered after commencement of the reperfusion, this should be done within five days after such commencement, more preferably within 24 hours after reperfusion commencement, and most preferably within 1 hour after beginning the reperfusion. In any case, the peptides of the invention must be administered before tissue or cell death has occurred.

BRIEF DESCRIPTION OF THE DRAWINGS

The following Figures all relate to the data generated in the Example, wherein:

FIG. 5 sets forth a series of amino acid sequences of peptides wherein the PXXP motifs are underlined and adjacent arginine residues are shown in bold type;

DETAILED DESCRIPTION OF THE PREFERRED EMBODIMENT

Figure 1:
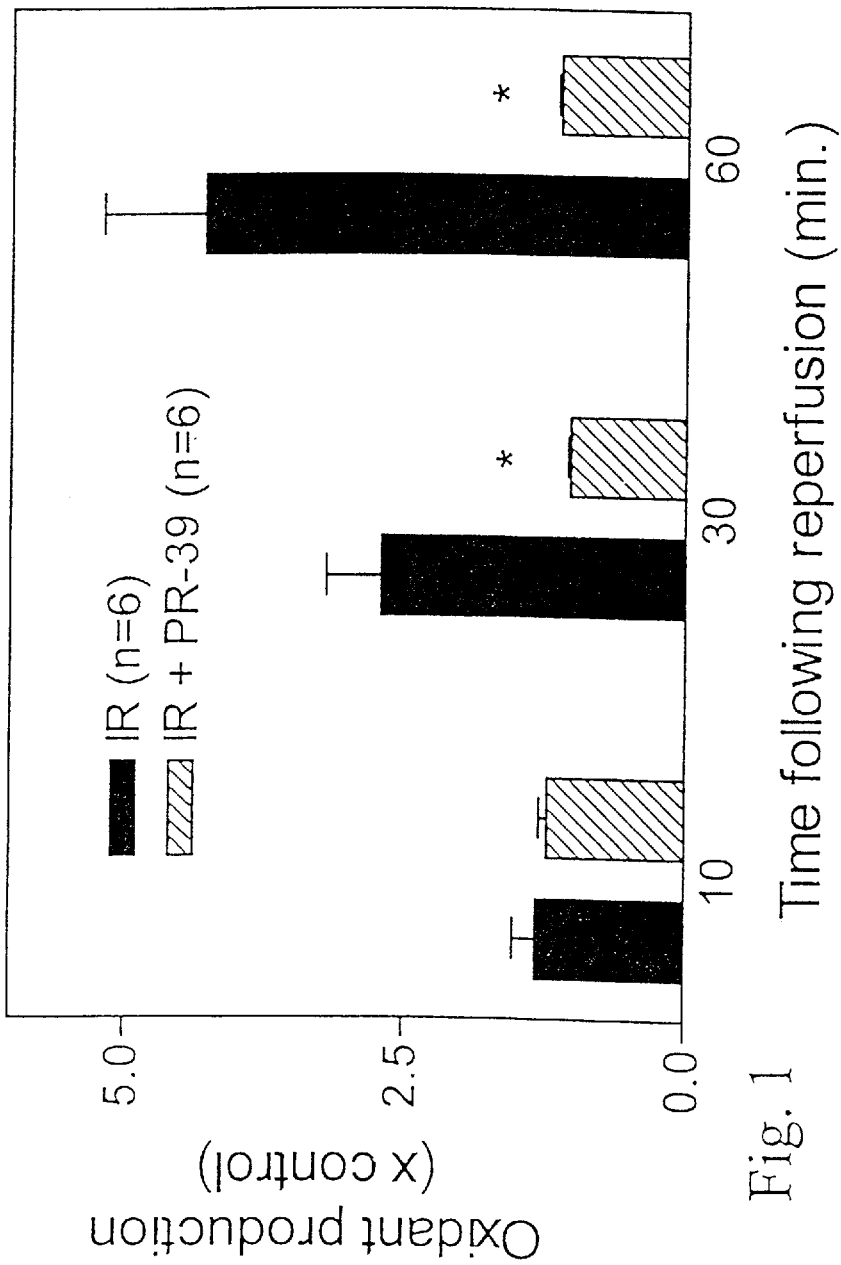
FIG. 1 is a graph setting forth the inhibition of reactive oxygen species after a surgical ischemia-reperfusion cycle in six surgically treated rats and six surgically treated rats also receiving 5 $\mu$M of the peptide PR-39 (SEQ ID NO: 1) pre-surgery, wherein the data are expressed as means+/−SEM and the starred data denotes differences from time-matched control, $p<0.01$.

The following examples set forth exemplary procedures and methods illustrating use of the present invention. It is to be understood that these examples are set forth by way of illustration only and nothing therein should be taken as a limitation upon the overall scope of the invention.

EXAMPLE 1

In this example, the efficiency of PR-39 (SEQ ID NO: 1) was tested in an in vivo model of reperfusion. Measurements of reactive oxygen release, neutrophil adherence to postcapillary venules and neutrophil emigration through venular endothelium, and vascular leakage were made in the presence and absence of PR-39 (SEQ ID No. 1). Control rats included animals which did not receive the peptide but were surgically treated, and animals which received neither the peptide nor the ischemic treatment.

In this example, male Sprague-Dawley rats weighing 220–250 g each were used. The rats were anesthetized by intraperitoneal injection of pentobarbital (30–40 mg/kg rat body weight) and the jugular vein of each rat was cannulated for reagent injection. The carotid artery of each rat was also cannulated for measurements of mean arterial blood pressure using a pressure transducer (Model P23a, Statham) and physiological recorder (Grass Instruments). Each animal was placed in a supine position on an adjustable microscope stage, and the abdomen was opened via a midline incision 2–3 cm long. The ileocecal portion of the mesentery was then gently exteriorized and placed on a clear Plexiglass viewing pedestal mounted in a bath. Throughout the experiments, the rat tissues were bathed in warmed bicarbonate-buffered saline bubbled with a gas mixture of 90% $N_2$ - 5% $CO_2$. Microvessels were observed using a microscope (Nikon Optiphoto) equipped with a 40×objective lens. The images were captured with a charge-coupled device camera (Model C2400-60, Hamamatsu Photonics) which was mounted on the microscope, projected onto a television monitor (Model PVM-2030, Sony) and recorded using a videocassette recorder (Model HS-U65, Mitsubishi). A video time-date generator (Model WJ-810, Panasonic) was used to project the time, date and stopwatch functions onto the monitor.

Single, unbranched venules with diameters between 25–35 μm and lengths longer than 150 μm (both measured with a video caliper, Microcirculation Research Institute, Texas A&M University) were selected for the studies.

After completion of the surgical preparation, the PR-39 (SEQ ID No. 1) peptide was administered to each animal via the jugular cannula and the animal was allowed to stabilize for thirty minutes. The PR-39 (SEQ ID No. 1) was administered at a dosage calculated to be about 5 μM in the vascular compartment, assuming a total blood volume of 6% of body weight. At the end of the stabilization period, the segment of intestine under study was subjected to 20 minutes of ischemia by gently clamping the superior mesenteric artery with a small, atraumatic vascular clamp. At the end of the ischemic period, an intravital, oxidation-sensitive dye, dihydrorhodamine 123, was injected via the jugular cannula for measurement of reactive oxygen production. The occlusion was then released and video data recording was performed at 10 minutes, 30 minutes and 60 minutes for oxidant production and for two 10-minute periods starting at 20 minutes and 50 minutes after release of the occlusion, respectively.

In more detail, generation of reactive oxygen levels were measured by the dihydrorhodamine 123 dye. This dye freely permeates through membranes thus penetrating cells, including neutrophils. Upon generation of reactive oxygen intermediates, the dye was converted to rhodamine 123 and emitted a fluorescent signal when excited at 488 nm; the intensity of the light signal was proportional to the amount of oxidant generated. Data were collected using a silicon-intensified target (SIT) camera.

The number of adherent and transmigrating leukocytes was determined off-line using videotaped images. A leukocyte was considered adherent to venular endothelium when it remained stationary for longer than 30 seconds. Adherent leukocytes were expressed as the number per 100 μm length of venule. The number of emigrating leukocytes were also determined off-line and were expressed as the number per microscopic field.

FIG. 1 is a graph depicting the results obtained in the comparative oxidant production tests. Oxidant production was significantly inhibited in the PR-39 (SEQ ID No. 1)-treated animals at the 30 minute time after resumption of mesenteric venular circulation, and even more so after 60 minutes.

Figure 2:
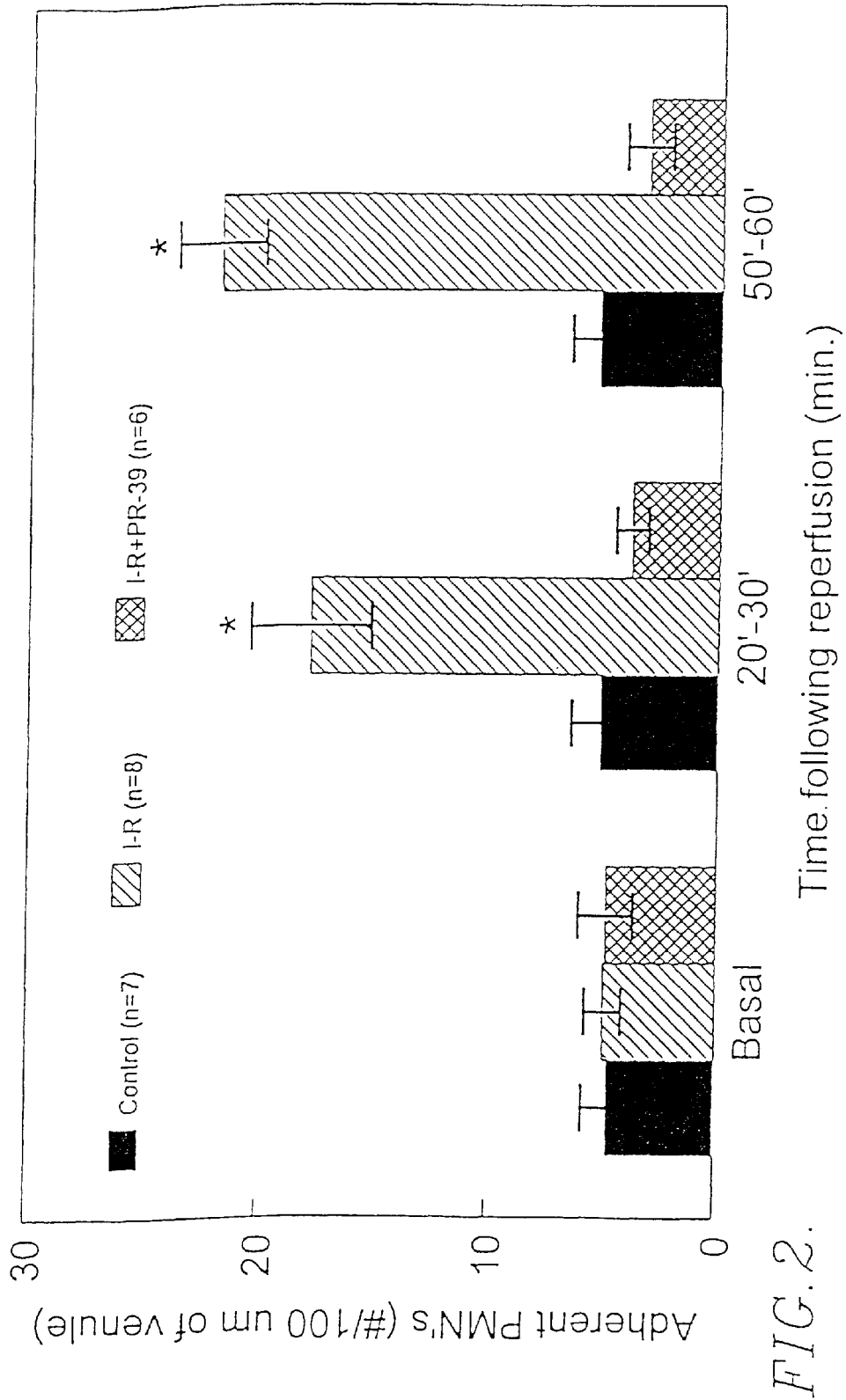
FIG. 2 is a graph setting forth the inhibition of leukocyte adherence to mesenteric venular endothelium after a surgical ischemia-reperfusion cycle in eight surgically treated rats and six surgically treated rats also receiving 5 $\mu$M of the peptide PR-39 (SEQ ID NO: 1) pre-surgery, compared to seven control rats neither surgically treated nor receiving the peptide, wherein the data are expressed as means+/−SEM and the starred data denotes differences from time-matched control, value $p<0.01$.
Figure 3:
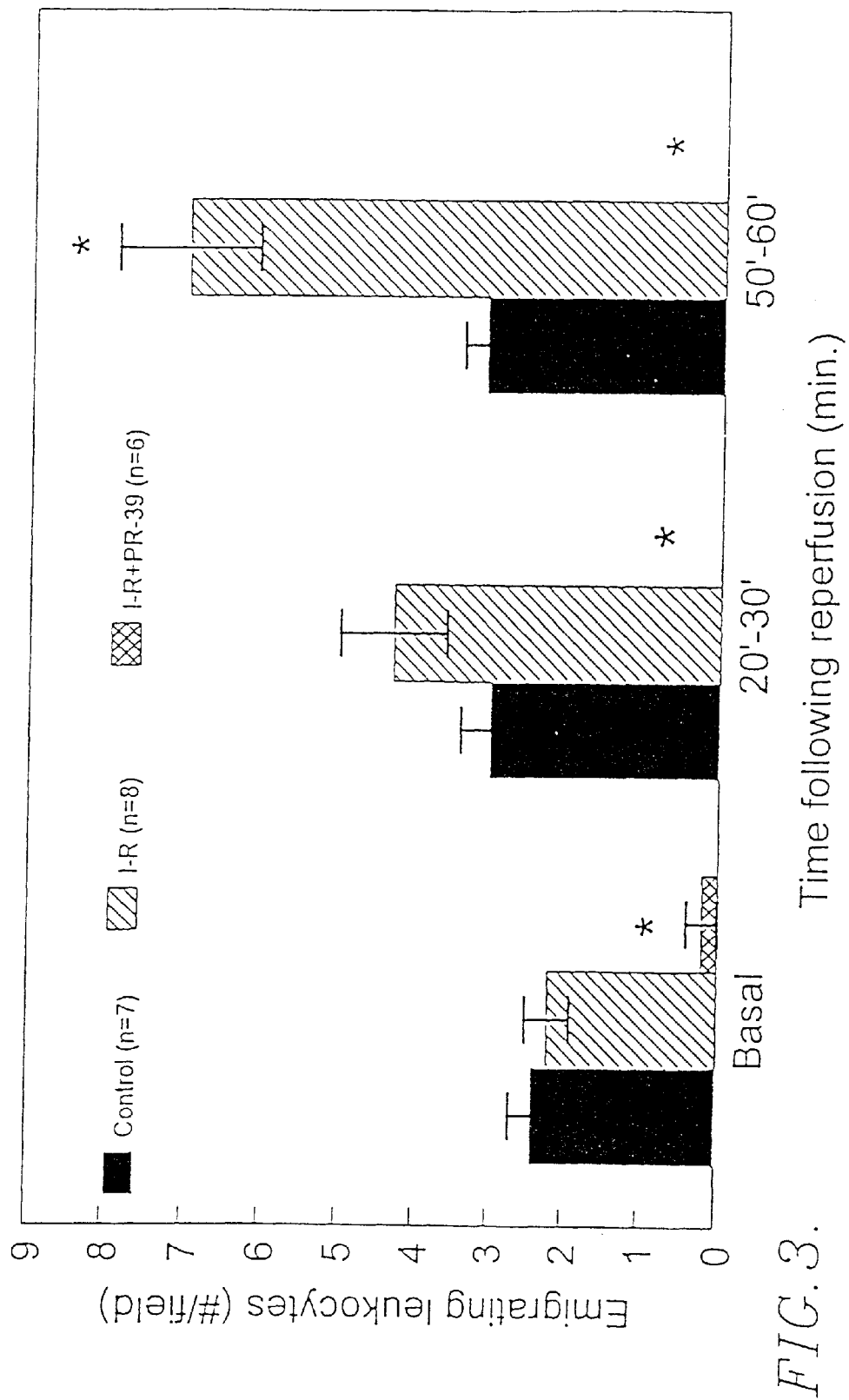
FIG. 3 is a graph setting forth the inhibition of leukocyte emigration through venular endothelium after a surgical ischemia-reperfusion cycle in eight surgically treated rats and six surgically treated rats also receiving 5 $\mu$M of the peptide PR-39 (SEQ ID NO: 1) pre-surgery, compared to seven control rats neither surgically treated nor receiving the peptide, wherein the data are expressed as means+/−SEM and the starred data denotes differences from time-matched control, value $p<0.01$.

Pretreatment with about 5 μM PR-39 (SEQ ID No. 1) peptide also blunted neutrophil adhesion to venular endothelium, resulting in no apparent endothelium neutrophil interaction in excess of basal levels (FIG. 2). PR-39 (SEQ ID No. 1) effects on transvascular neutrophil emigration were even more pronounced, with no migrating neutrophils observed at either post-release time point (FIG. 3). In addition, basal neutrophil emigration appeared to be diminished, indicating that PR-39 (SEQ ID No. 1) may affect some constitutive mechanism of neutrophil trafficking. It was also interesting that PR-39 (SEQ ID No. 1) downregulated both neutrophil adhesion and emigration, in light of a currently hypothesized scenario of the reperfusion cascade holds that non-NADPH oxidase sources of superoxide anion (such as xanthine oxidase) initiate reperfusion injury by generating neutrophil chemoattractants and upregulating cell adhesion mechanisms (Granger, DN, R Korthius (1995), Physiologic Mechanisms of Postischemic Tissue Injury. *Ann. Rev. Physiol.* 57:311–332).

PR-39 (SEQ ID No. 1) is believed to be the most potent endogenous downregulator of NADPH oxidase thus far discovered. The above in vivo data suggest that PR-39 (SEQ ID No. 1) eliminates or minimizes the reperfusion injury-induced adhesion and extravasation of neutrophils; in comparison, 2 μM adenosine caused reductions of only 65% and 32%, respectively in a cat mesenteric model. As a downregulator of reactive oxygen production, PR-39 (SEQ ID No. 1) thus compares favorably with adenosine treatment (complete prevention of oxidant release versus 20% reduction) (Grisham M, L Hernandez, D N Granger (1989), Adenosine Inhibits Ischemia Reperfusion-Induced Leukocyte Adherence and Extravasation. *Am. J. Physiol.* 257:HI334–HI339).

EXAMPLE 2

An assessment of vascular integrity was made by quantification of albumin leakage through mesenteric venules. Three groups of Sprague-Dawley rats (6 rats/group and respectively labeled control, I/R and I/R+PR-39) were obtained. Two of the groups (I/R and I/R+PR-39) were surgically prepared to occlude the superior mesenteric artery, and the I/R PR-39 (SEQ ID No. 1) group was treated with PR-39 (SEQ ID No. 1), all as described in Example 1. The control group was subjected to a similar surgical preparation, but without occlusion of the mesenteric artery or PR-39 (SEQ ID No. 1) administration. Fifty mg/kg fluorescein isothiocyanate-labeled bovine albumin was administered IV to each of the rats of each group, 15 min. prior to release of occlusion of the rats of the I/R and I/R+PR-39 (SEQ ID No. 1) groups. Fluorescence intensities within three segments of the venule under study ($I_v$) and in three adjacent areas of interstitium ($I_i$) were detected using a SIT camera (Model C-2400-08; Hamamatsu Photonics). Measurements were made at the basal, 20–30 min., and 50–60 min. time points using a computer-assisted digital imaging processor (NIH Image 1.35 on a Macintosh computer). An index of albumin leakage was expressed as the ratio of $I_i$ to $I_v$ at each time.

Figure 4:
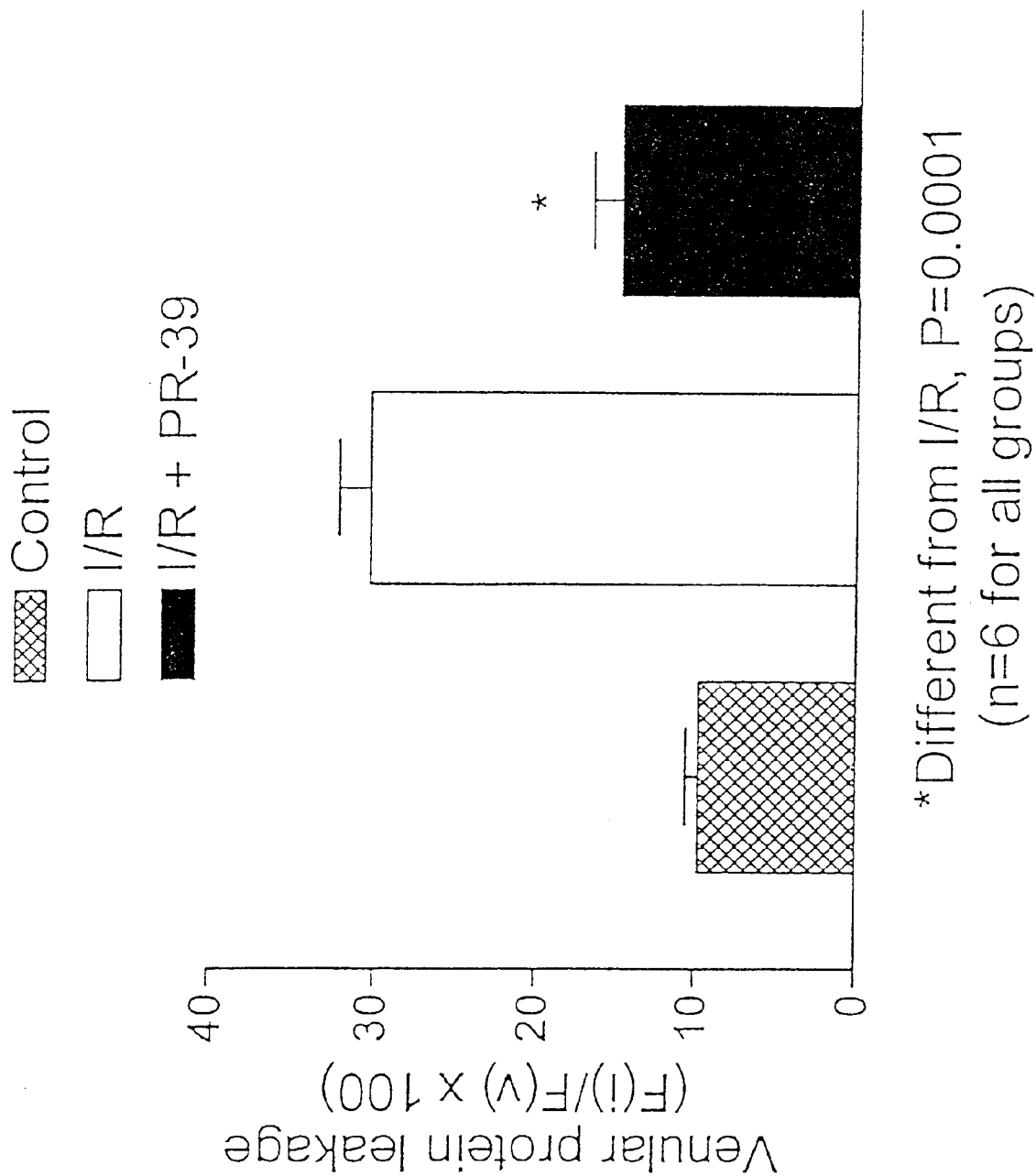
FIG. 4 is a graph setting forth venular protein leakage after a surgical ischemia-reperfusion cycle in PR-39 (SEQ ID No. 1) treated rats, wherein fluorescein-labeled albumin was administered to the rats prior to occlusion release and the ratio of the fluorescence intensity in the mesenteric artery and in adjacent regions of the interstitium was measured over time, in order to demonstrate that PR-39 (SEQ ID No. 1) reduces vascular degradation incident to ischemia-reperfusion.

As shown in FIG. 4, pretreatment of rats with PR-39 (SEQ ID No. 1) prevented loss of vascular integrity resulting from reperfusion injury. Thus, pretreatment with PR-39 (SEQ ID No. 1) blocks reperfusion-induced production of reactive oxygen, neutrophil adhesion and emigration, and loss of vascular integrity.

EXAMPLE 3

In this example, the effectiveness of a number of proline-rich peptides was determined in the context of inhibition of neutrophil superoxide anion production and inhibition of neutrophil chemotaxis.

Six peptides were tested in this example, namely PR-39 (SEQ ID No. 1), Bac5 (SEQ ID No. 7), rPR-26 (SEQ ID No. 8), Bac7 (SEQ ID No. 9), C7 (SEQ ID No. 10) and PF-1 (SEQ ID No. 11). The amino acid sequences of these peptides are set forth in FIG. 5, which also includes underlining of the PXXP motifs therein and shows adjacent arginine residues in bold type.

In one in vitro test, a "cell-free" oxidase assay was carried out using the necessary, reconstituted cell components making up NADPH oxidase. This assay is fully described in Shi et al., PR-39, a Proline-Rich Antibacterial Peptide That Inhibits Phagocyte NADPH Oxidase Activity, *Proc. Nat. Acad Sci.* USA, 93:6014–6018 (1996) which is incorporated by reference herein. Briefly, however, cell-free superoxide production was measured using 96-well plates and a Molecular Devices Therinomax microplate reader. Reactions (100 $\mu$l) contained $10^6$ cell equivalents of human neutrophil cytosol and $5\times10^5$ cell equivalents of deoxycholate-solubilized membranes prepared from human peripheral blood neutrophils. Reaction mixtures contained 50 mM potassium phosphate (pH 7), 0.2 mM acetylated cytochrome c, 4 mM $MgCl_2$, 1 mM EGTA, 10 $\mu$M FAD, I $\mu$M guanosine 5'-[$\gamma$-thio]triphosphate, and 200 $\mu$M NADPH. The reactions were initiated by addition of 40 $\mu$M arachidonic acid. Control reactions contained 5 $\mu$g of superoxide dismutase. Superoxide generation was calculated based on superoxide dismutase-inhibitable changes in cytochrome absorbance observed at 511 nm. The reactions were followed for 20 minutes after addition of arichidonic acid, with absorbance readings taken at 1-minute intervals. Maximum rates of superoxide generation were calculated from a linear least squares fit of 10 consecutive 1-minute data points. Determinations were based on reactions performed in triplicate.

Figure 6:
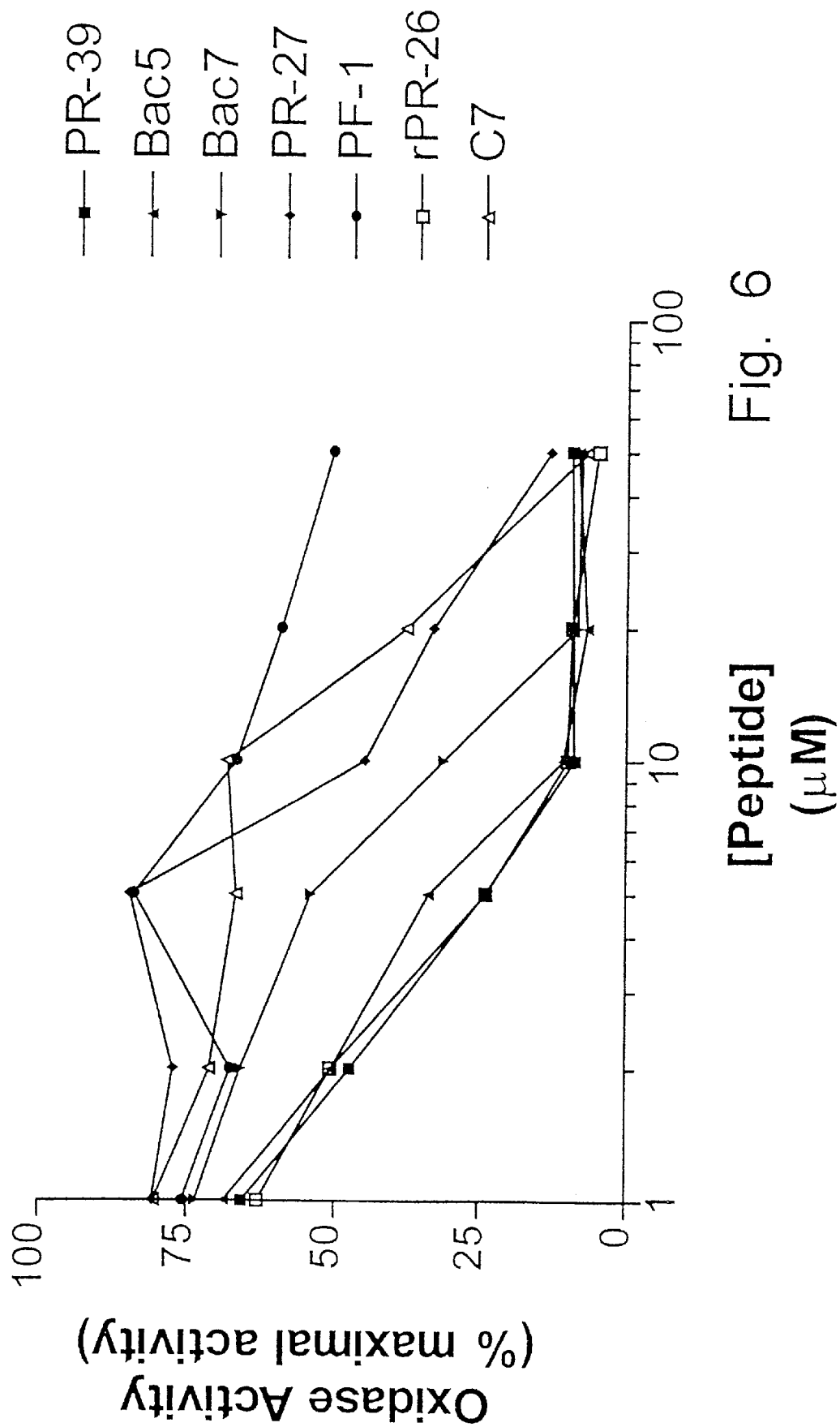
FIG. 6 is a graph showing the inhibition of neutrophil superoxide anion generation by PR-39 (SEQ ID No. 1) and other cationic, PXXP-containing peptides.

As set forth in FIG. 6, all of the peptides tested inhibited NADPH oxidase to some degree. Structure/function analysis suggests that greater inhibitory activity correlates best with increasing overall length of peptide, and also with the presence of multiple PXXP sequences (see FIG. 5). The least effective peptide in this set of experiments is PF-1 (SEQ ID No. 11), which consists of the first two decapeptide repeats of the antimicrobial peptide prophenin-1. PF-I (SEQ ID No. 11) contains only a single arginine, which lies C-terminal to the three PXXP motifs. Thus, these data indicate that peptides containing one or more PXXP sequences inhibit superoxide production by the NADPH oxidase. In addition, the presence of one or more basic residues such as arginine lying immediately adjacent to the PXXP motifs is preferred for effective inhibition.

The ability of four proline-arginine-rich peptides (PR-39 [SEQ ID No. 1], Bac5 [SEQ ID No. 7], Bac7 [SEQ ID No. 9], and C7 [SEQ ID No. 10]) to decrease oxidase activity in whole neutrophils was tested. In these experiments, superoxide anion production by neutrophils was determined by the superoxide dismutase-inhibitable reduction of ferricytochrome c.

Four samples were prepared for each animal: (1) neutrophils ($1\times10^6$ cells) in Hanks' balanced salt solution (HBSS; without phenol red) mixed with 100 $\mu$l (80 $\mu$M) of ferricytochrome c, 10 $\mu$l (0.1 $\mu$g) phorbol myristate acetate (PMA), and 100 $\mu$l (300 U) of superoxide dismutase (SOD); (2) cells treated with ferricytochrome c only; (3) cells treated with ferricytochrome c and PMA; and (4) cells treated with ferricytochrome c and SOD. The mixtures were incubated at 39° C. for 20 min. and then centrifuged at 4° C. (350×g) for 5 min. Cell-free supernatant (200 $\mu$l) was transferred to flat-bottom 96-well plates, and OD was read at 550 nm using HBSS as the blank. Production of superoxide anion was calculated using the following formula: OD of [(3+4)−(1+2)]×190.5=nm superoxide/1 $\times10^6$ cells/20 min.

Figure 7:
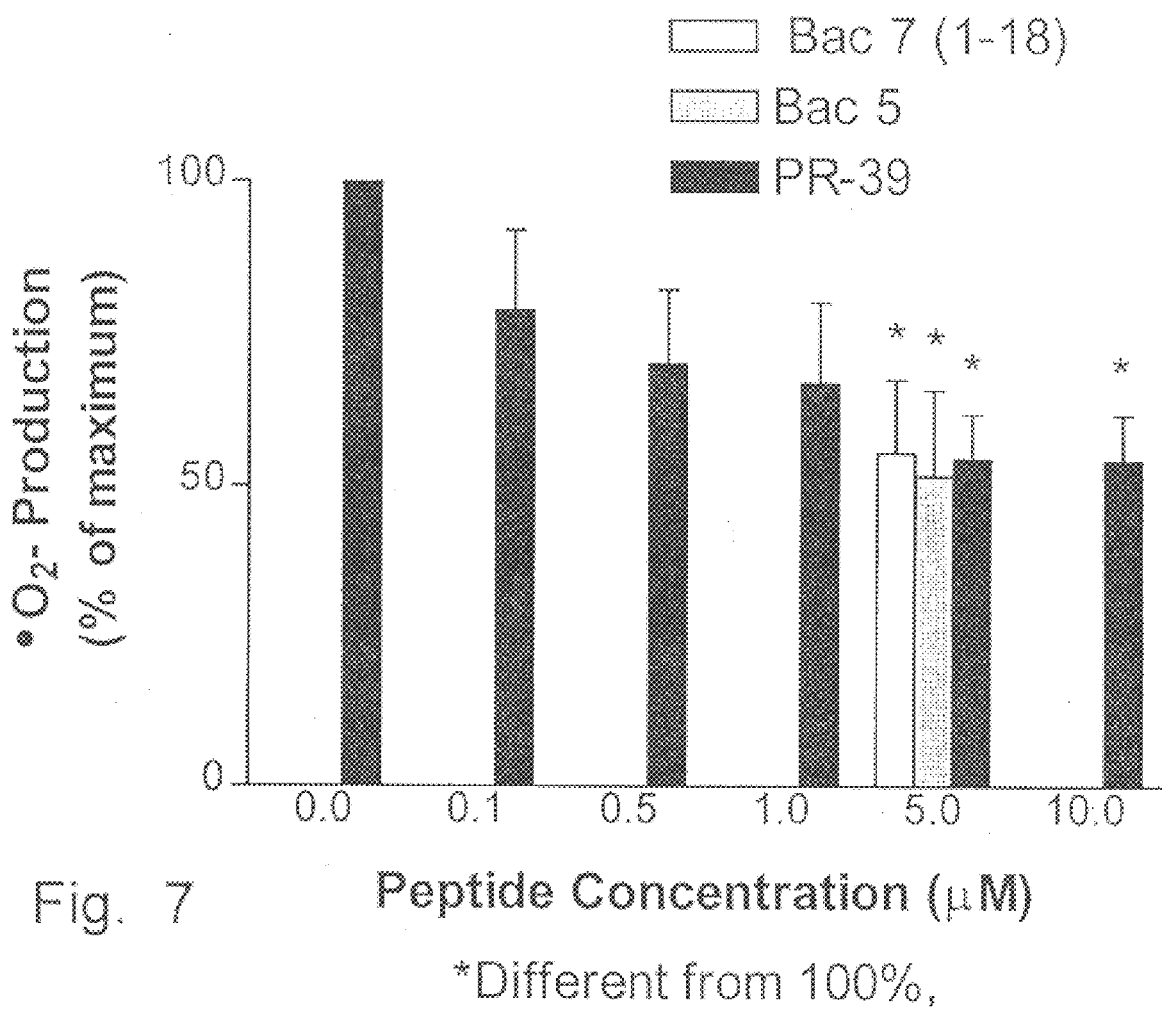
FIG. 7 is a graph showing the inhibition of superoxide anion generation in intact neutrophils by PR-39 (SEQ ID No. 1) and two other cationic, proline-rich, PXXP-containing peptides, Bac5 (SEQ No. 7) and Bac7 (SEQ ID No. 9)
Figure 8:
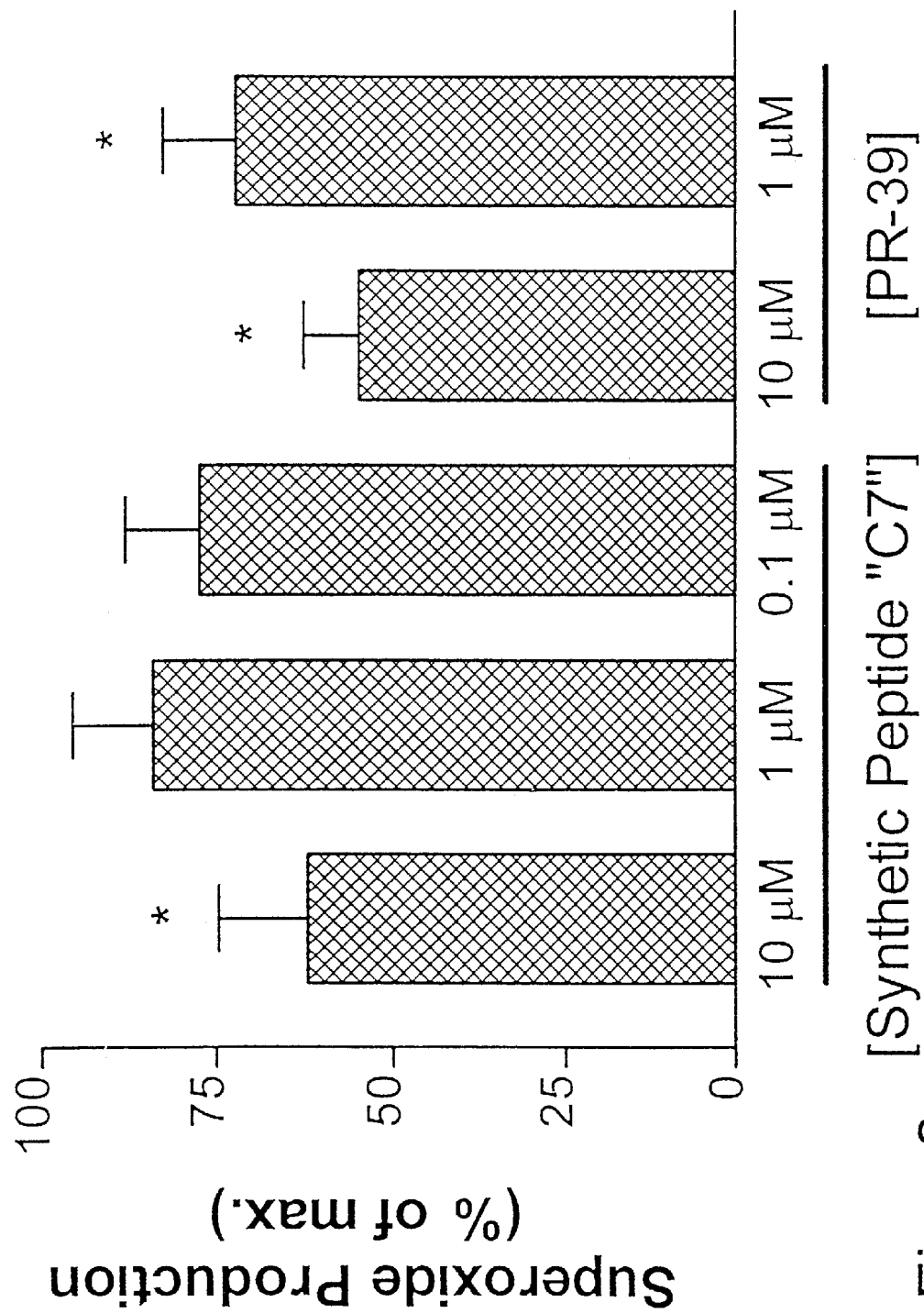
FIG. 8 is a graph depicting the inhibition of superoxide anion generation in intact human neutrophils by a non-naturally occurring, cationic, PXXP-containing peptide, C7 (SEQ ID No. 10)

As shown in FIGS. 7 and 8, all peptides tested inhibited neutrophil oxidase activity at concentrations ranging from 5–10 $\mu$M. These data indicate that oxidase inhibition is a widely held property of cationic, proline-rich peptides, and that this class of compounds are useful agents in the prevention of disease states that result from inappropriate neutrophil oxidase activity, such as reperfusion injury.

Figure 9:
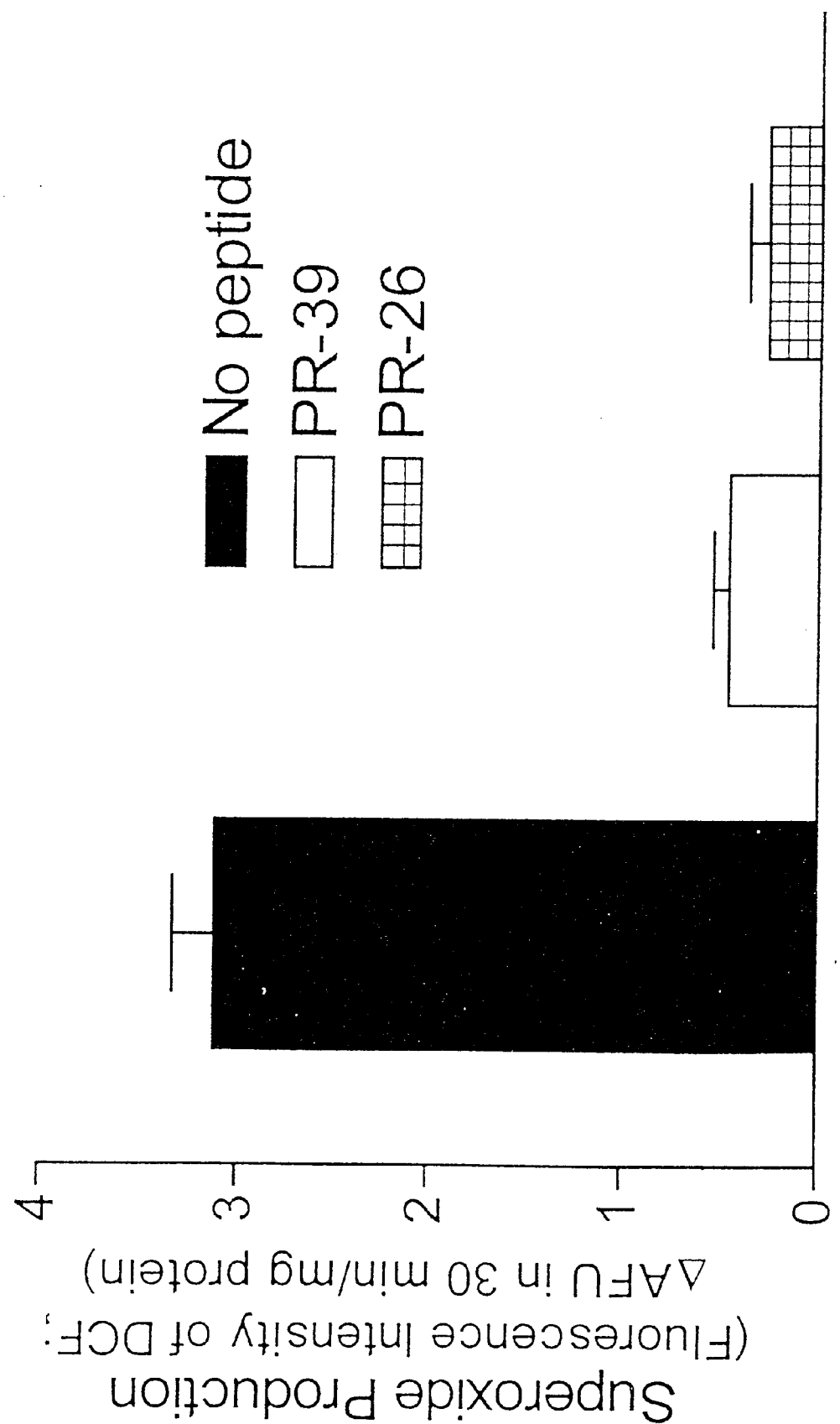
FIG. 9 is a graph illustrating the inhibition of superoxide anion production in bovine pulmonary artery endothelial cells using two cationic PXXP-containing peptides, PR-39 (SEQ ID No. 1) and PR-26 (SEQ ID No. 2)

PR-39 (SEQ ID No. 1) was also tested in a cell other than neutrophils, namely bovine pulmonary artery endothelial (BPAE) cells. In these cells, membrane depolarization induced by high $K^+$ treatment results in the production of superoxide anion by an endothelial NADPH oxidase enzyme that may be similar to the oxidase found in neutrophils. In these experiments, cultured BPAE cells were loaded with an oxidation-sensitive dye, dichlorodihydrofluorescein, then treated with high $K^+$, plus or minus PR-39 (SEQ ID No. 1) or PR-26 (SEQ ID No. 2), for 30 min. Cells were then scraped, pelleted, washed, and sonicated. Fluorescence of the supernatant was then measured to assess superoxide production. FIG. 9 shows that both PR-39 (SEQ ID No. 1) and PR-26 (SEQ ID No. 2) (10 $\mu$M) decrease oxidase activity in pulmonary endothelium.

The possibility that basic, proline-rich peptides might interfere with reperfusion injury by mechanisms other than through NADPH oxidase blockade was also investigated. In order for neutrophils to inflict post-reperfusion inflammatory tissue damage, they must first adhere to vascular endothelium, then migrate into tissues, where oxidative lesions occur. Neutrophil attachment and migration during reperfusion induced inflammation are mediated by a number of different compounds released by target tissues; among these compounds is the phospholipid metabolite, platelet activating factor (PAF).

A microchemotaxis assay was used to examine the effect of PR-39 (SEQ ID No. 1) and another basic, PXXP-containing antimicrobial peptide, Bac5 (SEQ ID No. 7), on neutrophil chemotaxis alone and in combination. Whole blood was obtained from 250–350 g Sprague-Dawley rats by terminal cardiac puncture into acid citrate dextrose solution. Neutrophils were isolated by dextran sedimentation, followed by density-gradient centrifugation and hypotonic lysis to remove contaminating erythrocytes. Micropore filters (5 $\mu$M-pore polycarbonate membrane) were used to separate the lower and upper chambers of the microchemotaxis chamber. Attractants to be tested were diluted in RPMI medium and added (35 $\mu$l) to the lower wells of the chamber; 50 $\mu$l of the cell suspension ($5\times10^6$ cells/$\mu$l) was added to the upper chamber. Chambers were placed in a humidified atmosphere of 5% $CO_2$ in air at 37° C. for 40 min. Cells on the underside of the filters were fixed, stained, and counted using high-power brightfield microscopy. For each sample, four test wells containing chemoattractant were used. The total number of neutrophils in five fields was counted for each well. All results are expressed as a chemotaxis index defined as the number of cells migrating in response to RPMI alone.

Figure 10:
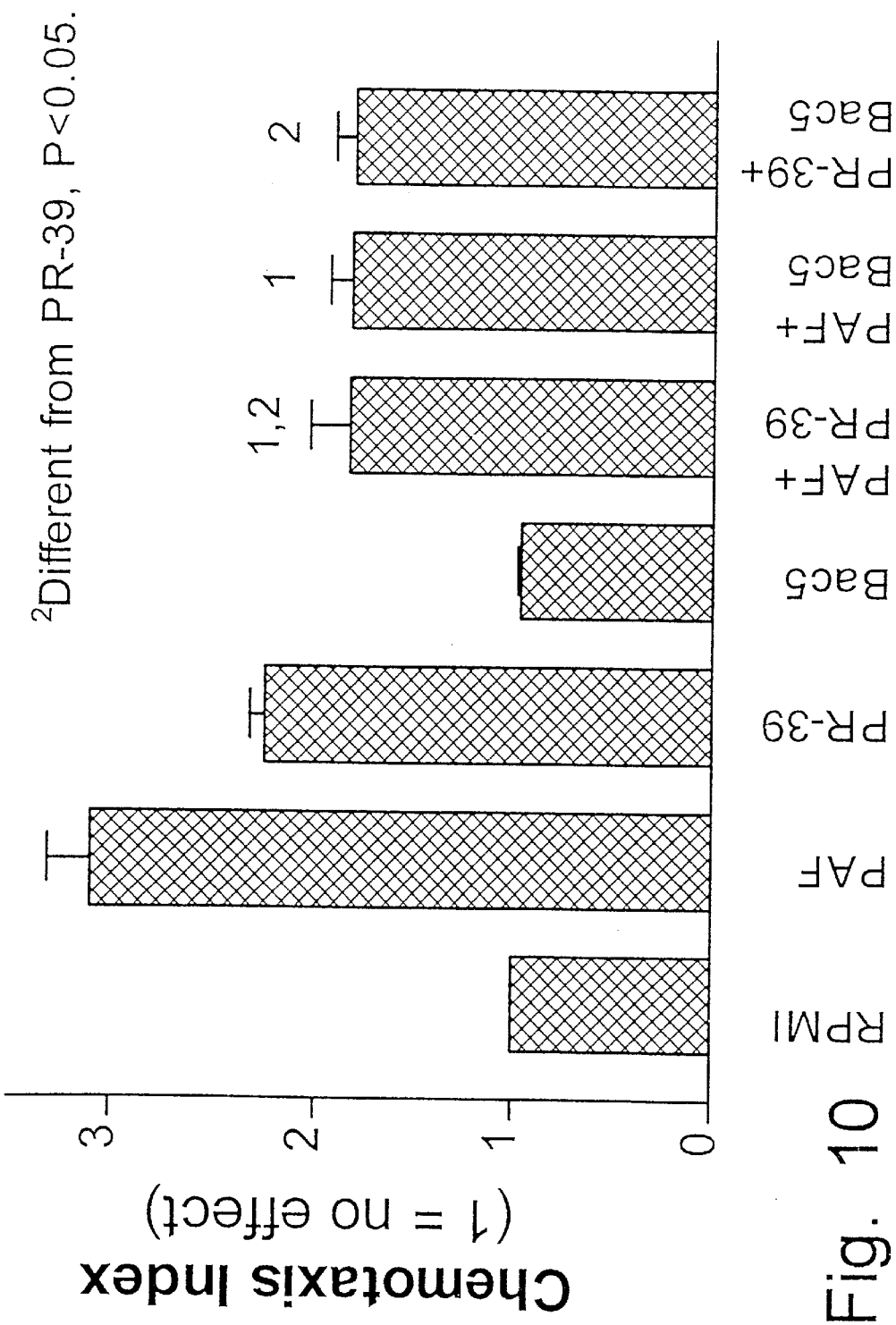
FIG. 10 is a graph illustrating the inhibition of neutrophil chemotaxis by combinations of chemoattractants, PAF (100 ng/ml), PR-39 (SEQ ID No. 1) (10 $\mu$M) and Bac5 (SEQ ID No. 7) (10 $\mu$M).

Results of these studies are shown in FIG. 10. It is apparent that although PAF and PR-39 (SEQ ID No. 1) are chemotactic for neutrophils when examined alone, all three are capable of acting as inhibitors of the others when examined in combination.

We claim:

1. An in vivo method of reducing reperfusion injury in a mammal resulting from reperfusion of a temporarily occluded blood vessel of the mammal, said method comprising the steps of administering into the mammal's bloodstream a reperfusion injury-reducing amount of a peptide having up to about 50 amino acid residues, at least 65% of said residues being made up of the sum of the proline and arginine residues therein, and allowing said peptide to come into effective contact with said blood vessel for minimizing reperfusion injury, said administering step occurring within up to about one hour after said reperfusion.

2. The method of claim 1, said peptide being selected from the group consisting of the peptides of SEQ ID NOS: 1–11.

3. The method of claim 1, said peptide being selected from the group consisting of the peptides of SEQ ID NOS: 1–2.

4. The method of claim 1, said peptide being SEQ ID NO: 1.

5. The method of claim 1, including the step of administering said peptide into said mammal's bloodstream prior to the commencement of reperfusion.

6. The method of claim 1, including the step of administering the peptide into said mammal's bloodstream during reperfusion.

7. The method of claim 1, said reperfusion occurring as a result of a surgical procedure.

8. The method of claim 1, said reperfusion occurring subsequent to spontaneous occlusion.

9. The method of claim 1, said peptide having at least one —PXXP— amino acid sequence therein, where P is proline and X is any amino acid.

10. The method of claim 9, said peptide having at least four —PXXP— amino acid sequences therein.

11. The method of claim 10, some of said —PXXP— sequences being substantially contiguous.

12. The method of claim 9, said peptide having one or more basic amino acid residues located within six residues from both the starting and terminal proline residues of the —PXXP— sequence.

13. The method of claim 12, said basic amino acid residues located within three residues from both the starting and terminal proline residues of the —PXXP— sequence.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (xi) SEQUENCE DESCRIPTION: SEQ ID NO:1:

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

(2) INFORMATION FOR SEQ ID NO:2:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:2:

Arg Arg Arg Pro Arg Pro Pro Tyr Leu Pro Arg Pro Arg Pro Pro
1               5                   10                  15

Phe Phe Pro Pro Arg Leu Pro Pro Arg Ile
            20                  25

(2) INFORMATION FOR SEQ ID NO:3:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:3:

Arg Pro Arg Pro Pro Pro Phe Phe Pro Pro Arg Leu Pro Pro Arg Ile
1               5                   10                  15

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:4:

Arg Arg Arg Pro Arg Pro Pro Tyr Leu Pro Arg Pro Arg Pro
1               5                   10

(2) INFORMATION FOR SEQ ID NO:5:

```
    (i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:5:

Arg Pro Pro Pro Phe Phe Pro
1               5

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:6:

Pro Pro Arg Leu Pro Pro Arg Ile
1               5

(2) INFORMATION FOR SEQ ID NO:7:

(i) SEQUENCE CHARACTERISTICS:
        (A) LENGTH: 43 amino acids
        (B) TYPE: amino acid
        (D) TOPOLOGY: linear (ii) MOLECULE TYPE: peptide (xi) SEQUENCE DESCRIPTION: SEQ ID NO:7:

Arg Phe Arg Pro Pro Ile Arg Arg Pro Pro Ile Arg Pro Pro Phe Tyr
1               5                  10                  15

Pro Pro Phe Arg Pro Pro Ile Arg Pro Pro Ile Phe Pro Pro Ile Arg
                20                  25                  30

Pro Pro Phe Arg Pro Pro Leu Gly Pro Phe Pro
            35                  40

(2) INFORMATION FOR SEQ ID NO:8:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:8:

Ile Arg Pro Pro Leu Arg Pro Pro Phe Phe Pro Pro Arg Pro Arg
1               5                  10                  15

Pro Leu Tyr Pro Pro Arg Pro Arg Arg
            20                  25

(2) INFORMATION FOR SEQ ID NO:9:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:9:

Arg Arg Ile Arg Pro Arg Pro Pro Arg Leu Pro Arg Pro Arg Pro Arg
```

-continued

```
1               5               10              15
Pro Leu Tyr Cys
            20

(2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:10:

Arg Arg Gly Pro Arg His Pro Gln Thr Arg Leu Pro Arg Pro Leu Pro
1               5                   10                  15

Asp Pro (2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:11:

Ala Phe Pro Pro Pro Asn Val Pro Gly Pro Arg Phe Pro Pro Pro Asn
1               5                   10                  15

Phe Pro Gly Pro Arg
            20
```